United States Patent [19]

Harrington et al.

[11] 4,057,646

[45] Nov. 8, 1977

[54] SUBSTITUTED OR UNSUBSTITUTED P-ALKANOYL TOLUENES AS MALE ANTI-FERTILITY AGENTS

[75] Inventors: Francis E. Harrington, Mendham; Robert S. Ho, Denville, both of N.J.

[73] Assignee: Sandoz, Inc., E. Hanover, N.J.

[21] Appl. No.: 717,525

[22] Filed: Aug. 25, 1976

[51] Int. Cl.² ............................................. A61K 31/12
[52] U.S. Cl. .................................................... 424/331
[58] Field of Search ......................................... 424/331

[56] References Cited

U.S. PATENT DOCUMENTS 3,941,888   3/1976   Houlihan et al. .................... 424/331

Primary Examiner—Frederick E. Waddell
Attorney, Agent, or Firm—Gerald D. Sharkin; Robert S. Honor; Timothy G. Rothwell

[57] ABSTRACT

Certain substituted or unsubstituted p-alkanoyl toluenes, e.g., p-alkanoyl toluene, are useful as male anti-fertility agents.

5 Claims, No Drawings

SUBSTITUTED OR UNSUBSTITUTED P-ALKANOYL TOLUENES AS MALE ANTI-FERTILITY AGENTS

This invention relates to the pharmaceutical activity of p-alkanoyl toluenes. More particularly, this invention concerns the use of substituted or unsubstituted p-alkanoyl toluenes in the treatment of fertility. The invention also relates to pharmaceutical compositions containing these compounds as an active ingredient thereof.

The active agents with which this invention is concerned may be represented by the following structural formula:

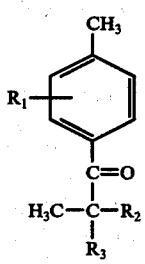

where
- $R_1$ represents hydrogen, halo having an atomic weight of about 19 to 36, and straight chain lower alkoxy, i.e., straight chain alkoxy having 1 to 4 carbon atoms, e.g., methoxy, ethoxy, isopropoxy or the like, and
- $R_2$ and $R_3$ each independently represent alkyl having 1 or 2 carbon atoms, i.e., methyl or ethyl.

The compounds of formula (I) above are known and may be prepared according to methods disclosed in the literature from known materials. The present invention contemplates only the novel use of such compounds as male anti-fertility agents.

The compounds of formula (I) are useful because they possess pharmacological activity in animals. In particular, the compounds of formula (I) are useful as male anti-fertility agents.

The test was conducted in adult male and non-parous female Wistar rats. Both males and females were housed individually in open wire bottom cages in a room with a 14:10 light/dark photoperiod. A normal Purina pelleted rat chow ration was fed to all 26 males for 5 weeks followed by a 3-week period of a ground Purina rat ration. Immediately following the latter ration, a similar ration containing the test compound at a concentration of 0.1 percent was administered to half the males (13) for 8 weeks. The remaining male rats continued to receive the ground Purina rat chow ration during this 8-week period. Following the ration containing the test compound, all males received the regular pelleted rat chow for the remaining 11 weeks of the study. The female rats received the regular pelleted rat chow throughout the study.

Matings were then conducted on Monday, Tuesday, and Wednesday of each week. Each male was exposed individually to a proestrus female on each day until a mating had occurred. Verification of copulation was based upon the presence of sperm cells in the vaginal smear. If the male failed to copulate on these 3 days, he was no longer exposed to a female until the following week.

For the first 15 weeks of the study, the presence of vaginal plugs under the cages was noted but not recorded for each male. During the last 12 weeks of the study, the presence of vaginal plugs under each male cage was recorded.

Litter size was based upon females autopsied between days 19 - 21 of pregnancy, during the first 20 weeks of the study. The number of viable and non-viable fetuses was recorded. During the last 7 weeks, litter size was based upon the number of offspring present at parturition. In addition to viability data, the number of males and females delivered was recorded.

Males in both treatment groups were found to be normally fertile during the pretreatment period. Normal sperm cells were observed in the vaginal smears and litter sizes for the two groups of males were similar.

The reproductive pattern among control males during the period of time (weeks 9 - 16) that the test compound was present in the diet was similar to that observed during the pretreatment period. However, among males exposed to the drug, significant changes in various reproductive parameters were noted. Within 6 days of exposure to the drug the number of females found to have sperm cells in the vaginal smears had declined, and by the 8th week of exposure (week 16), none of the vaginal smears contained sperm cells. During weeks 10 through 15, the sperm cells observed in the various vaginal smears were generally abnormal and fewer in number than for control animals. Vaginal plugs were observed under the cages of both control and treated males on weeks 9 through 15, but they were not recorded. During the last week of exposure to the drug in the diet, the presence of vaginal plugs under each male's cage, in both control and treated groups, was observed and recorded. This latter observation is critical since it demonstrates that males were copulating (i.e., libido maintained) even though sperm cells were absent.

Nine of 13 males sired litters after 6 days exposure to the test compound, but only one male sired a litter in each of the following 2 weeks. Thus, by the fourth week of exposure to the drug, none of the treated males sired a litter.

It was not until the fifth week, following withdrawal of the drug from the diet, that sperm cells were first noted in two of the females exposed to the treated males. The number of sperm cells observed were greatly reduced and no litters were produced at this time. Though vaginal plugs were observed under the cage of each of the treated males 6 weeks after exposure to the test compound, only nine of the females contained sperm cells in the vaginal smear, and four of these females delivered litters. During the next 2 weeks, sperm cells were observed in the vaginal smears of all the females exposed to drug treated males except for one.

For such use, the compounds of formula (I) may be administered orally or parenterally as such or admixed with conventional pharmaceutical carriers. They may be administered orally in such forms as tablets, dispersible powders, capsules, soft gelatin capsules, preferably soft gelatin capsules, and emulsions, and parenterally as emulsions, e.g., a sterile injectable emulsion. The compositions for oral use may contain one or more conventional adjuvants, such as sweetening agents, flavoring agents, coloring agents, and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, lubricating agents, e.g., magnesium stearate, stearic acid and talc, and absorbing agents, such as colloidal silicone dioxide. The tablets may be uncoated or coated by known techniques to delay disintegration and absorption in the gastrointestinal tract and thereby provide a sustained action over a longer period. Similarly, suspensions and emulsions may contain the active ingredient in admixture with any of the conventional excipients utilized by the preparation of such compositions, e.g., suspending agents such as methylcellulose, tragacanth and sodium alginate; wetting agents, such as lecithin, polyoxyethylene stearate and polyoxyethylene sorbitan monooleate; and preservatives, such as ethyl-p-hydroxybenzoate. Capsules may contain the active ingredient admixed with a inert solid diluent, e.g., calcium carbonate, calcium phosphate and kaolin. Soft gelatin capsules may contain the active ingredient in admixture with conventional pharmacuetical excipients, e.g., inert carriers, such as vegetable oils (soybean oil, corn oil, and the like) polyethylene glycol derivatives or mineral oils. The injectable compositions are formulated as known in the art. These pharmaceutical preparations may contain up to about 90 percent of the active ingredient in combination with the carrier or adjuvant.

In general, satisfactory results are obtained when the compounds of formula (I) are administered at a daily dosage of about 2.0 to about 300 milligrams per kilograms of animal body weight p.o., preferably given in divided doses one to four times a day, or in sustained release form. For most large mammals, the total daily dosage is from about 120 milligrams to about 4200 milligrams. Dosage forms suitable for internal use comprise from about 40 milligrams to about 2100 milligrams of the active compound in intimate admixture with a solid or liquid pharmaceutically acceptable carrier or diluent.

Compounds of formula (I) which can be used as the active ingredient include the following:
 a. 2-chloro-4-pivaloyl toluene;
 b. 2-methoxy-4-pivaloyl toluene; or
 c. p-pivaloyl toluene, the latter being especially preferred.

A representative formulation suitable for oral administration is a tablet, capsule, or soft gelatin capsule prepared by standard tabletting or encapsulating techniques which contains the following and may be administered two to four times a day in the treatment of fertility.

EXAMPLE 1

| Ingredient | Weight (mg.) capsule |
|---|---|
| p-pivaloyl toluene | 100 |
| tragacanth | — |
| lactose | 300 |
| corn starch | — |
| talcum | — |
| magnesium stearate | — |
| | 400 mg. |

EXAMPLE 2

| Ingredient | tablet | capsule | soft gelatin capsule |
|---|---|---|---|
| p-pivaloyl toluene | 100 | 100 | 100 |
| polyvinylpyrrolidone | 15 | — | — |
| lactose | 282.5 | 346 | — |
| corn starch | 25 | — | — |
| talcum | 15 | — | — |
| colloidal silicon dioxide | 50 | 50 | — |
| magnesium stearate | 2.5 | — | — |
| stearic acid | — | 4 | — |
| soybean oil | — | — | 300 |
| | 500 mg. | 500 mg. | 400 mg. |

The following pharmaceutical compositions are formulated with the indicated amount of active agent using conventional techniques. The injectable emulsion, the oral liquid suspension, and the oral liquid emulsion represent formulations useful as unit doses and may be administered in the treatment of fertility. The injectable emulsion is suitable for administration once or twice a day whereas the oral liquid suspension and the oral liquid emulsion is suitabley administered two to four times per day for this purpose.

EXAMPLE 3

| Ingredient | Weight (mg.) Oral liquid suspension |
|---|---|
| p-pivaloyl toluene | 100 |
| magnesium aluminum silicate | 47.5 |
| flavor | q.s. |
| color | q.s. |
| methyl paraben, U.S.P. | 4.5 |
| propyl paraben, U.S.P. | 1.0 |
| polysorbate 80 (e.g., Tween 80), U.S.P. | 5 |
| sorbitol solution, 70%, U.S.P. | 2,500 |
| buffer agent to adjust pH for desired stability | q.s. |
| water | q.s. to 5 ml. |

EXAMPLE 4

| Ingredient | Sterile injectable emulsion | Oral liquid emulsion |
|---|---|---|
| p-pivaloyl toluene | 200 | 100 |
| sodium, carboxy methylcellulose, U.S.P. | — | 12.5 |
| polyvinylpyrrolidone | 5 | — |
| benzoyl alcohol | 0.01 | — |
| sodium chloride | to be adjusted to an isotonic concentration | — |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | 1 | 5 |
| sorbitol solution, 70% U.S.P. | — | 2,500 |
| buffer agent to adjust pH for desired stability | q.s. | q.s. |
| water | q.s. for injection q.s. to 1 ml. | q.s. to 5 ml. |

The preferred pharmaceutical compositions from the standpoint of preparation and ease of administration are soft gelatin capsules containing from about 100 to 200 milligrams of the active ingredient.

What is claimed is:

1. A method of controlling fertility in male animals, which comprises administering to a male animal in need of said treatment an anti-fertility effective amount of a compound of the formula:

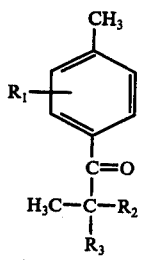

where
R₁ represents hydrogen, halo having an atomic weight of about 19 to 36, or straight chain lower alkoxy, and
R₂ and R₃ each independently represent alkyl having 1 to 2 carbon atoms.

2. The method of claim 1 in which the compound is:

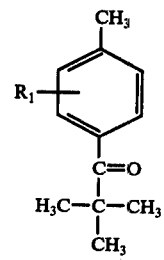

where R₁ is as defined in claim 1.

3. The method of claim 1 in which the compound is p-pivaloyl toluene.

4. The method of claim 1, wherein the compound is administered orally at a daily dosage of from about 120 milligrams to about 4200 milligrams.

5. The method of claim 1, wherein the compound is orally administered in a unit dosage form comprising from about 40 milligrams to about 2100 milligrams per unit dosage.

* * * * *